(12) United States Patent
Szeles

(10) Patent No.: US 7,781,486 B2
(45) Date of Patent: Aug. 24, 2010

(54) PUNCTUAL STIMULATION THERAPY

(76) Inventor: Josef Constantin Szeles, Glanzinggasse 5/7, A-1190 Vienna (AT)

( * ) Notice: Subject to any disclaimer, the term of this patent is extended or adjusted under 35 U.S.C. 154(b) by 1027 days.

(21) Appl. No.: 10/578,164

(22) PCT Filed: Nov. 4, 2004

(86) PCT No.: PCT/AT2004/000390

§ 371 (c)(1),
(2), (4) Date: Aug. 31, 2006

(87) PCT Pub. No.: WO2005/041948

PCT Pub. Date: May 12, 2005

(65) Prior Publication Data

US 2007/0135522 A1 Jun. 14, 2007

(30) Foreign Application Priority Data

Nov. 4, 2003 (AT) .............................. A 1750/2003

(51) Int. Cl.
*A61K 31/198* (2006.01)
*A61N 1/00* (2006.01)
*A61H 39/02* (2006.01)
*A61B 17/34* (2006.01)

(52) U.S. Cl. ................. 514/561; 514/567; 600/548; 606/189; 607/42

(58) Field of Classification Search ............ None
See application file for complete search history.

(56) References Cited

U.S. PATENT DOCUMENTS

| | | | |
|---|---|---|---|
| 4,331,145 A | | 5/1982 | Winter |
| 4,439,452 A | * | 3/1984 | Ehrenpreis et al. ........... 514/561 |
| 4,646,744 A | * | 3/1987 | Capel ........................ 607/58 |
| 5,084,007 A | * | 1/1992 | Malin et al. .................. 604/20 |
| 6,197,329 B1 | * | 3/2001 | Hermelin et al. ............ 424/441 |
| 6,955,873 B1 | * | 10/2005 | Blum ........................... 435/6 |

FOREIGN PATENT DOCUMENTS

| | | |
|---|---|---|
| EP | 0 004 040 | 9/1979 |
| WO | WO 90/05560 | 3/1990 |
| WO | WO 91/01756 | 2/1991 |

OTHER PUBLICATIONS

Josefson et al. Rheumatology. May 2003; 42: 1149-1154.*
*Acupuncture & Electro-Therapeutics Res.*, Int. vol. 7—1982—pp. 157-172—"D-Phenylalanine and Other Enkephalinase Inhibitors as Pharmacological Agents: . . . " by Seymour Ehrenpreis, Ph.D.—XP009043539.
*Acupuncture & Electro-Therapeutics Res.*, Int., vol. 10—1985—pp. 203-208—"Pharmacology of Enkephalinase Inhibitors: Animal and Human Studies" by Seymour Ehrenpresis, Ph.D.—XP009043546.
*Pain*, 8 (1980) pp. 231-236—"A Combined Treatment with D-Amino Acids and Electro-Acupuncture Produces a Greater Analgesia Than Either Treatment Alone; Naloxone Reverses These Effects" by Richard S.S. Cheng and Bruce Pomeranz—XP002316290.
Database Biosis [on line] Biosciences Information Service, Philadelphia, PA, US, 1991, Kalyuzhnyi L V et al: "The Effect of an Enkephalinase Blocker on Acupuncture Results in Acupuncture-Sensitive and Acupuncture-Resistant Rabbits" XP002316291.
Ehrenpreis S: "D-phenylalanine and other enkephalinase inhibitors as pharmacological agents: Implications for some important therapeutic application" Accupuncture and Electro-Therapeutics Research 1982 United Kingdom, vol. 7, No. 2-3, 1982, pp. 157-172, XP009043539 p. 163, paragraph 2—p. 164, paragraph 1 (to follow).

* cited by examiner

*Primary Examiner*—Shanon A Foley
(74) *Attorney, Agent, or Firm*—Collard + Roe, P.C.

(57) ABSTRACT

The invention relates to the use of a sterile aqueous solution of a substance inhibiting the enzymatic decomposition of endogenous opioide neuropeptides, especially enkephalins, for producing a preparation provided for intravenous infusion, in order to intensify the action of punctual stimulation therapy carried out with an electrical current. One such substance is e.g. D-phenylalanine. In cases that are difficult to treat, pain can be effectively reduced or stopped by infusion of the preparation.

3 Claims, No Drawings

PUNCTUAL STIMULATION THERAPY

CROSS REFERENCE TO RELATED APPLICATIONS

Applicant claims priority under 35 U.S.C. §119 of Austrian Application No. A 1750/2003 filed Nov. 4, 2003. Applicant also claim priority under 35 U.S.C. §365 of PCT/AT2004/000390 filed Nov. 4, 2004. The international application under PCT article 21(2) was not published in English.

Very good relief of existing pain can be achieved by means of punctual stimulation, in which electrical current is supplied by way of needle electrodes stuck into the skin, whereby these needle electrodes are placed, in particular, at specifically sensitive points of an outer ear, in the case of the predominant number of patients treated with such stimulation. In most cases, pain reduction by several stages of the VAS scale (Visual Analog pain Scale; 0 no pain; 1-3 slight pain, 4-6 severe pain; 7-10 intolerable pain) can be achieved; in many cases, complete freedom from pain can be achieved. Different patients do not respond to such stimulation, or respond only to a slight degree, and the pain reduction that can be achieved with such punctual stimulation is often insufficient in the case of very severe pain.

The present invention shows a way to intensify the effect of the aforementioned punctual stimulation, in order to achieve good pain reduction even in the case of patients who do not respond to this punctual stimulation, or respond only to a slight degree, and in the case of patients who are suffering from very severe pain.

For this purpose, the invention provides the use of a sterile aqueous solution of a substance that inhibits the enzymatic decomposition of endogenous opioid neuropeptides, for the production of a preparation intended for intravenous infusion, to intensify the effect of a punctual stimulation therapy, in which electrical current is supplied by way of needle electrodes stuck into the skin. With the infusion of an infusion solution structured in such a manner, it is possible to achieve a good stimulation effect in the sense of pain reduction, and extensive pain reduction that goes all the way to freedom from pain, even in the case of very severe pain, in the case of patients who did not respond or responded only insufficiently to the punctual stimulation previously. By means of the use of the preparation provided for intravenous infusion, the enzymatic decomposition of the opioid neuropeptides activated by the punctual stimulation, such as beta-endorphins, enkephalins, endomorphins, dynorphin, and orphonin-Q, is inhibited.

Preferably, it is provided that for the production of the preparation provided for intravenous infusion, a sterile aqueous solution having a content of a substance that inhibits enzymatic decomposition of endogenous opioid neuropeptides, particularly D-phenylalanine, of at least 5 g/L is used. The preparation obtained in this manner demonstrates good tolerance and, simultaneously, good decomposition inhibition.

An advantageous variant is characterized in that a sterile aqueous solution having a content of D-leucine of at least 5 g/L is used.

Another variant that offers advantages with regard to the effect spectrum of decomposition inhibition is characterized in that a sterile aqueous solution of D-phenylalanine and D-leucine having a sum content of at least 5 g/L is used.

An embodiment in which the tolerance perception during infusion of the preparation is improved is characterized in that a sterile aqueous solution additionally containing an anti-emetic is used.

The present invention also creates a method for punctual stimulation therapy, in which electrical current is supplied by way of needle electrodes stuck into the skin, whereby supplementally, a preparation that intensifies the effect of this stimulation, which contains a substance that inhibits the enzymatic decomposition of endogenous opioid neuropeptides, is administered in the form of an intravenous infusion. In this way, it is possible to achieve a good effect with regard to rapid onset of effect and an intensification of the effect of pain reduction, all the way to elimination of pain, and to do so even in the case of patients who do not respond or respond only to a slight degree to punctual stimulation that takes place without the aforementioned infusion. The method is practically low in side effects and causes neither respiratory depression nor any detrimental influence on the cardiovascular system.

In the case of an advantageous configuration of the method in terms of dosage and good decomposition inhibition, an aqueous solution containing D-phenylalanine is administered in the form of an intravenous infusion. Another advantageous variant provides that an aqueous solution containing D-leucine is administered in the form of an intravenous infusion. To achieve a broad spectrum of effect of decomposition inhibition, it is advantageous if an aqueous solution containing D-phenylalanine and D-leucine is administered in the form of an intravenous infusion. In the case of intravenous administration of a solution of D-phenylalanine, it is advantageous if an amount of more than 0.1 g per kilogram of body weight of the person being treated is administered. The administration of D-phenylalanine preferably takes place in the form of a solution having a concentration of at least 5 g/L. This is advantageous for decomposition inhibition.

With regard to the decomposition inhibition to be achieved, of the opioid neuropeptides released during punctual stimulation, the flow rate of the infusion can be selected within a comparatively broad range. Low flow rates are generally perceived as being more comfortable. The flow rate can be coordinated with how the person being treated feels during the infusion. This coordination is facilitated by adding an anti-emetic to the infusion solution. Coordination of the flow rate of the infusion to the effect that the duration of the infusion lasts at least one hour is generally advantageous for the patient's well-being and also for the interaction with the punctual stimulation, in the sense of decomposition inhibition.

Preferably, it is provided that the intravenous infusion is carried out during the punctual stimulation, which takes place with the supply of electrical current. This results in a particularly good interaction of the infusion with the punctual stimulation. It is also advantageous, in this connection, for a rapid onset of effect, if the intravenous infusion is started at least 10 min before the start of the punctual stimulation.

If the punctual stimulation is carried out by means of supplying current by way of needle electrodes stuck into sensitive points of both ears, extensive pain reduction, all the way to elimination of pain, can be achieved even in the case of very severe pain, and in this connection, the punctual stimulation can also be controlled very well.

For the treatment of severe and chronic pain, it is often advantageous if the treatment is carried out on several consecutive days, and in this connection, an infusion that lasts at least one hour and punctual stimulation are carried out on each of these days.

The pain reduction achieved with the method according to the invention generally lasts from several days to several months. An extension of effect can often be achieved, in simple manner, in that punctual stimulation on one ear, without infusion, is carried out after one of more treatment procedures carried out with infusion and punctual stimulation on both ears.

It is often also advantageous if punctual stimulation on one ear, without infusion, is carried out on one or more days before the punctual stimulation on both ears, to be carried out with infusion, or if several punctual stimulations on one ear, without infusion, are carried out.

With regard to the punctual stimulation procedure that takes place within the framework of the method according to the invention, it is advantageous if stimulation at first takes place at high frequency, in the range of 50 to 500 Hz, in the course of the punctual stimulation procedure, in each instance, and subsequently, stimulation takes place at a low frequency, in the range of 2 to 20 Hz. It is often also advantageous for more rapid pain reduction to perform stimulation intermittently, at high frequency, in the range of 50 to 500 Hz, and at low frequency, in the range of 2 to 20 Hz.

According to another aspect, the present invention relates to a set comprising a sterile aqueous solution of a substance that inhibits the enzymatic decomposition of endogenous opioid neuropeptides and a punctual stimulation therapy device, as well as the use of this set for pain reduction or elimination of pain. Examples of punctual stimulation therapy devices are familiar to a person skilled in the art, particularly from WO 90/05560 A.

EXAMPLES

Female Patient, 60 Years Old

Carcinoma patients with generalized metastases usually receive palliative pain therapy with opioids, depending on the degree of severity according to the classification of the WHO. In this severe case, it was not possible to achieve an even halfway tolerable situation with regard to pain, never mind freedom from pain, with medications. Since the patient was not free of pain, walking was only possible with great difficulty and with assistance. Furthermore, the doses of pain medication and opioids were so high that her sensory system was greatly dulled.

Punctual stimulation was carried out with the following treatment sequence:

On each of three consecutive days, punctual stimulation on both ears, with simultaneous intravenous infusion of a substance that inhibits the enzymatic decomposition of endogenous opioid neuropeptides, was carried out. Afterwards, punctual stimulation was carried out without infusion for the four subsequent days, by means of a small device worn by the patient, to supply power to needle electrodes that are stuck into the skin on one ear. This sequence was repeated several times, in coordination with the patient's need for pain reduction. In the case of punctual stimulations carried out with simultaneous infusion, electrical current was supplied to needle electrodes that were stuck into sensitive points of both ears. A sterile aqueous solution containing 20 g/L D-phenylalanine was administered as the infusion, whereby a total amount of D-phenylalanine of 200 to 300 mg/kilogram of body weight was administered during every treatment procedure. On the first days of the three-day sequences, in each instance, the infusion was started at least 10 min before the punctual stimulation. The flow velocity of the infusion was selected in accordance with an infusion period of 2.5 to 5 h.

During the course of each treatment procedure, pain reduction, which went all the way to freedom from pain, was rapidly achieved. After completion of each treatment procedure, the freedom from pain was maintained for some time, after which a slight increase in pain occurred. The time span of freedom from pain was increased by means of the treatment procedures performed with stimulation on both ears and infusion. This status was extended by means of the subsequent stimulation on one ear, performed without infusion, up to the next three-day sequence.

In this manner, pain reduction that went as far as possible, all the way to complete freedom from pain, was achieved, with good mobility of the patient, and no dulling of her sensory system occurred.

Female Patient, 45 Years Old

Chronic pancreatitis cyst for the past eight years; operated twice up to now. Severe pain attacks for the past two months. Also therapy-resistant back pain. VAS-9.8. Medication: opiates, Buscopan, etc., not free of pain despite this. Body weight 39 kg. Lost 11 kg recently. Frequent vomiting, nausea. Operation for resection of the pancreas head planned.

Admission to clinic. Punctual stimulation carried out without infusion, by means of power supply to needle electrodes that are stuck into one ear, over a period of four days. Pain reduction achieved in this manner. Subsequently, punctual stimulation by means of power supply to needle electrodes that are stuck in both ears, and simultaneous intravenous infusion of an aqueous solution containing 15 g/L D-phenylalanine, in an amount of 250 mg/kg of body weight. An anti-emetic was also added to the solution. Duration of infusion about 3 h. During the course of this treatment, pain reduction all the way to freedom from pain (VAS-0). After 8 days, discharge from the clinic—free of symptoms, no vomiting, no nausea, no medication. At discharge, application of a device for punctual stimulation on one ear, without infusion, as mentioned above, for four days. Freedom from symptoms remains maintained during this stimulation period. On the following days, slight pain in the abdominal region, in individual instances. Three days after completion of the prior stimulation, again application of a device for a stimulation lasting four days—immediately clear relief. After this stimulation, again increase in pain, but tolerable without medication. After another three days, again application of such a device—free of symptoms. After removal of the device, again slight increase in pain, whereby the number of pain attacks and their intensity has decreased in comparison with previously. After several days, again a device applied for stimulation on one ear, lasting for four days—free of symptoms. After removal of the device, slow increase in pain to VAS-3-4. Ten days after removal of the device, again punctual stimulation on two ears, with intravenous infusion, as explained above. Pain reduction to VAS-0. Afterwards complete freedom from pain for 48 h. Subsequently slow increase in pain up to maximum VAS-4. Two weeks after punctual stimulation on both ears, again application of a device for four days of stimulation on one ear without infusion—free of symptoms during stimulation. Another two weeks later, again application of such a device—free of symptoms during stimulation. Afterwards, more severe pain again in paraumbilical region, in individual instances. Again, application of a device as mentioned—free from symptoms during the stimulation. Later, sudden increase in pain. Therefore one week later, again punctual stimulation on both ears, with infusion. VAS-0. During the subsequent weeks, weekly application of a device for four days of punctual stimulation on one ear. During this stimulation, pain reduction to VAS-0. Even during a subsequent three-week break in therapy, no medication, no nausea, no vomiting. Good state of well-being, good appetite, body weight now 47 kg. Continuation of the therapy with application of the device for four days of stimulation on one ear, at one-week and two-week intervals. The need for an operation no longer seems to exist.

Male Patient, 64 Years Old

Cirrhosis of the liver (transplant required). Painful lumbar ischialgia, resistant to therapy, for the past 20 years, VAS 9.5.

Primary clinical question as to whether the patient can be freed from pain by means of punctual stimulation and infusion, because post-operative mobilization after a transplant is absolutely necessary for its success. Therefore immediately punctual stimulation by means of power supply to needle electrodes that were stuck into both ears and, at the same time, intravenous infusion of an aqueous solution containing 20 g/L D-phenylalanine, in an amount corresponding to 300 mg/kg of body weight. Infusion period 3 h.

During the course of this stimulation, pain reduction from VAS 9.5 to VAS 0. Patient leaves the outpatient clinic free of pain and without dulling of the sensory system, feeling well. Continuation of this therapy by means of punctual stimulation on one ear, without infusion, over a period of four days. Afterwards, still completely free of pain. Over the course of the subsequent months, slight increase in pain, up to finally VAS-6. Therefore after another five months, again punctual stimulation on both ears, with infusion, as described above. Again, complete freedom from pain achieved. Subsequently, again punctual stimulation on one ear, without infusion, over a period of four days.

Female Patient, 70 Years Old

Constant pain in the left abdomen and in the shoulder for quite some time. VAS 9-10.

Punctual stimulation (without infusion) for four days, by means of power supply to needle electrodes that are stuck into one ear, resulted in clear pain relief from VAS-9 to VAS-2 in the shoulder and to VAS-0 in the left abdomen. The abdominal pain did not occur again afterwards. The other treatments were only necessary due to the shoulder pain. After three more days without therapy, back to VAS-7. Again, punctual stimulation (four days) as described above resulted in further pain relief. After another three days (without therapy), VAS-5. Ten days later, VAS-5. Now punctual stimulation by means of power supply to needle electrodes that were stuck into both ears and, at the same time, intravenous infusion of a solution containing 20 g/L D-phenylalanine, in an amount corresponding to 300 mg/kg of body weight. Infusion period: 3.5 h.

Reduction of pain during this treatment to VAS-0. After completion of this punctual stimulation on both ears, with infusion, continuation of the treatment by means of electrical punctual stimulation on one ear, without infusion over a period of four days. During this time, no kind of pain at all. After another three days (without therapy), about VAS-5. This pain status remained essentially the same subsequently, i.e. cut in half since the beginning of therapy. One month afterward, punctual stimulation on one ear again, without infusion, four days, pain reduction from VAS-7 to VAS-0. After another three days, still free of pain with regard to back and shoulder pain. Ten days later, punctual stimulation on both ears with infusion, as explained above. Complete freedom from pain. Only after six weeks, increase to VAS-2, but no pain medication required, good mobility. Again, punctual stimulation on one ear, without infusion—freedom from pain.

Female Patient, Born 1967

For months, intolerable pain (VAS-10) in the right ankle. Severely disabled, unable to walk. Two crutches required. Opiates for pain relief. Strong sleep aids to allow sleep at night. Subsequent diagnosis: bone marrow edema caused by viral infection. No weight on leg and cortisone therapy. Reduction in the edema did not result in improvement of the pain status in the foot region. Additionally, severe back pain (VAS-8).

Punctual stimulation without infusion for a period of four days on one ear results in clear pain relief of the back pain from VAS-8 to VAS-5, but no relief of the pain in the foot region. Subsequently, punctual stimulation therapy with stimulation by means of needle electrodes stuck into both ears, to which electrical current was supplied and, at the same time, administration of an intravenous infusion of a sterile solution containing 15 g/L D-phenylalanine. The infusion amount was coordinated with the administration of 250 mg/kg of body weight of the patient. The flow velocity was adjusted in accordance with an infusion period of 3 h.

This punctual stimulation procedure resulted in complete freedom from pain. The patient was able to leave the outpatient clinic moving freely, without crutches. On the same day, a device for four days of punctual stimulation on one ear, without infusion, was applied. During this stimulation (for four days), essentially free of pain.

After several days, pain increasingly occurred again. After one week, VAS-6. Again, punctual stimulation with simultaneous infusion, as described above, was carried out, over the course of which complete freedom from pain (VAS-0) occurred again.

It was planned to continue this pain therapy at foreseeably weekly intervals, until the virus disease had run its course. After two sessions of four days of stimulation performed on one ear, no further therapy was required. The patient was free of pain.

Male Patient, 46 Years Old

After ganglion operation on the left hand, intolerable pain (VAS-10), which gave cause for a first re-operation, but occurred again about three weeks after the latter, and occurred again immediately after a second re-operation. Pulling, stabbing pains all the way into the shoulder. Infusion therapy did not produce any improvement. About one year after the ganglion operation, neuropathic pain, neuropathic tendinopathy, VAS-10-opiates. Subsequent laser operation was able to relieve the neuropathic pain, for some of the time, but stabbing pain in the region of the first and second fingers remained. Sudek. Six weeks after laser operation, dull pain in the lower arm. Ten weeks after laser operation, more pain—tendinopathy, pressure sensitivity. Fifteen weeks after laser operation, pulling pain in thumb. Later, again pain VAS-8-9, in individual cases. Infiltration of Scandicaine yields improvement to VAS-6. Later, pain again: thumb, left wrist, thumb base joint painful to pressure. Twenty months after the aforementioned laser operation, more laser operations (desservation and laser bonding). Post-operatively, after two weeks, burning pain in the first interdigital fold—radiating all the way into the shoulder. Pain remains. After another five months, VAS-8 in the left lower arm. After another five months, burning at the thumb base joint and the wrist. After another three months, further deterioration of the pain state. Burning pain also in the lower arm. Continuously, only unsatisfactory pain relief can be achieved by means of therapy with medications.

Sixteen months after second laser operation, four days of electrical punctual stimulation on one ear, without infusion. No pain reduction could be achieved. Subsequently, punctual stimulation on both ears, with simultaneous intravenous infusion of a solution containing 20 g/L D-phenylalanine. The punctual stimulation took place by means of power supply to needle electrodes stuck into both ears. Infusion period 4 h. Infusion amount in accordance with 300 mg/kg of body weight. Over the course of this treatment, complete freedom from pain (VAS-0) was achieved, starting from VAS-10. The complete freedom from pain made it possible to move the hand without problems. The freedom from pain lasted for three days. Afterwards, increase in pain to VAS-4. Subsequently, additional punctual stimulation as described above was planned.

The invention claimed is:

1. A method for punctual stimulation therapy, comprising the following steps:
    carrying out puntual stimulation by supplying electrical current to a patient by way of needle electrodes stuck into sensitive points on both ears of the patient;
    administering a preparation that intensifies the effect of said stimulation, said preparation containing a substance that inhibits enzymatic decomposition of endogenous opioid neuropeptides, said preparation being administered in the form of an intravenous infusion; and
    thereafter carrying out punctual stimulation on one ear, without infusion.

2. The method according to claim 1, wherein on each of several consecutive days, the infusion is administered for at least one hour and the punctual stimulation by way of needle electrodes stuck into sensitive points of both ears is carried out on each of several consecutive days, and wherein the step of punctual stimulation on one ear without infusion is carried out after one or more treatments with said steps of administering the infusion and carrying out punctual stimulation on both ears.

3. A method for punctual stimulation therapy, comprising the following steps:
    carrying out at least one punctual stimulation on one or more days by supplying electrical current to a patient by way of needle electrodes stuck into sensitive points on one ear of the patient;
    and subsequently carrying out a treatment comprising:
        administering a preparation that intensifies the effect of said stimulation, said preparation containing a substance that inhibits enzymatic decomposition of endogenous opioid neuropeptides, said preparation being administered in the form of an intravenous infusion, and
        carrying out punctual stimulation by supplying electrical current to a patient by way of needle electrodes stuck into sensitive points on both ears of the patient.

* * * * *